United States Patent [19]

Polefka et al.

[11] Patent Number: 5,180,577

[45] Date of Patent: Jan. 19, 1993

[54] STABILIZED BIS BIGUANIDE/ANIONIC ACTIVE INGREDIENT COMPOSITIONS

[75] Inventors: Thomas G. Polefka; Deborah S. Sanai, both of Somerset; Brian S. Jannone, Basking Ridge, all of N.J.

[73] Assignee: Colgate-Palmolive, New York, N.Y.

[21] Appl. No.: 594,502

[22] Filed: Oct. 9, 1990

[51] Int. Cl.⁵ .................. A61K 7/16; A61K 7/18; A61K 7/22

[52] U.S. Cl. ...................... 424/52; 424/49; 424/54

[58] Field of Search .................. 424/49-58

[56] References Cited

U.S. PATENT DOCUMENTS

| Re. 32,300 | 12/1986 | Gorman et al. | 514/635 |
|---|---|---|---|
| 3,934,002 | 1/1976 | Haefele | 424/54 |
| 3,937,805 | 2/1976 | Harrison | 424/54 |
| 3,937,807 | 2/1976 | Haefele | 424/54 |
| 4,025,616 | 5/1977 | Haefele | 424/54 |
| 4,051,234 | 9/1977 | Gieske et al. | 424/54 |
| 4,059,624 | 11/1977 | Harrison | 424/54 |
| 4,130,637 | 12/1978 | Bauman | 424/54 |
| 4,420,484 | 12/1983 | Gorman et al. | 514/332 |

FOREIGN PATENT DOCUMENTS 2442712  3/1976  Fed. Rep. of Germany ........ 424/54

OTHER PUBLICATIONS

Nowak GA. 69:9929YH (1968).
L'Orange et al. GA 84:184919V (1976) of Ger. Offen. 2, 442, 712 Mar. 25, 1976.
Sugiyama et al. GA 111:1402435 (1989) of JP63211217 Sep. 2, 1988.

Primary Examiner—Shep K. Rose
Attorney, Agent, or Firm—Paul Shapiro; Robert C. Sullivan

[57] ABSTRACT

An oral composition is provided and a method for making the same. The composition comprises a cationic antibacterial agent, an anionic active ingredient and, as a stabilizing agent, a stabilizing quantity of a betaine surfactant.

12 Claims, No Drawings

STABILIZED BIS BIGUANIDE/ANIONIC ACTIVE INGREDIENT COMPOSITIONS

BACKGROUND OF THE INVENTION

This invention relates to compositions comprising bis biguanide antimicrobial agents in combination with one or more anionic active ingredients. In particular, this invention relates to the employment of bis biguanide as the antimicrobial agent in an antiplaque oral composition wherein an anionic active ingredient is also employed.

The bis biguanide compounds of which this invention is concerned are described in German patent application No. P2,332,383 published on Jan. 10, 1974 and have the generic formula

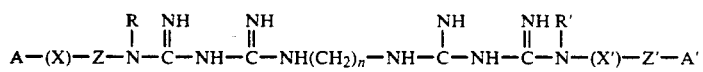

wherein A and A' each represent either (1) a phenyl radical which optionally is substituted by one alkyl or alkoxy group containing from 1 to about 4 carbon atoms, a nitro group, or a halogen atom; (2) an alkyl group containing from 1 to about 12 carbon atoms; or (3) alicyclic groups containing from 4 to about 12 carbon atoms; wherein X and X' each represent an alkylene radical containing from 1 to 3 carbon atoms; wherein Z and Z' each can be either 0 to 1; wherein R and R' each represent either hydrogen, or alkyl radical containing from 1 to about 12 carbon atoms, or an aralkyl radical containing from 7 to about 12 carbon atoms; wherein n is an integer from 2 to 12 inclusive; and wherein the chain $(CH_2)_n$ may optionally be interrupted by oxygen or sulfur atoms, aromatic nuclei, etc.

These compounds have long been known to have antimicrobial properties, and in particular have been known to be useful in oral compositions as antimicrobial antiplaque agents. The employment of these compounds in commercial products has been severely hampered by virtue of at least two properties of the bis biguanides: to wit, they are highly cationic and are known to stain dental surface.

The cationic nature of these compounds has greatly inhibited their use. This, for example, in British Patent 825,5777 published Dec. 16, 1959 it is described that these highly cationic antimicrobials, when incorporating in conventional dentifrice compositions were not effectively absorbed onto dental surfaces whereas mere aqueous compositions containing the antimicrobial were effective. The British patent then discloses that the culprit in reducing the affectivity of these cationic bis-biguanide antimicrobials was the presence in such dental compositions of anionic detergents such as sodium lauryl sulphate, sodium lauryl sarcosinate and soap. These surfactants have traditionally been incorporated into oral compositions to provide the composition with foaming properties. Taught, therefore, in this British Patent is the use of non-anionic surfactants, e.g. cationic, non-ionic or anpholytic detergents. By avoiding the use of anionic detergents, the inactivation of the cationic bis biguidine is said to have been avoided.

Unfortunately, the simple solution of avoiding anionic surfactants is not applicable to the problem faced by modern formulators who wish to employ the cationic bis biguanides in oral compositions. While an abundance of non-anionic surfactants are now available, it is also desirable to incorporate into oral compositions a host of newly developed or newly employed compounds for therapeutic, prophylactic, aesthetic or organoleptic purposes and many of these compounds are anionic in such compositions. Thus, for example, modern oral compositions contain anti-tartar e.g. phosphoric compounds which are highly anionic; anticaries agents such as fluorides which are highly anionic; antistaining agents to counteract the staining properties of the cationic antimicrobial agents, which antistaining agents are likewise anionic; and the like. Not surprisingly, these anionic agents tend to associate with the cationic antimicrobials and in the extreme, precipitate out of solution, thereby rendering either the antimicrobial or the anionic agent ineffective. Accordingly, in many cases, the formulator has been forced to seek substitutes for the otherwise highly effective bis-biguanides.

This problem has been raised, for example, in the specification of U.S. Pat. No. 3,934,002 issued to John Wilkins Haefele on Jun. 20, 1976 and incorporated herein by reference. The specification is directed toward providing an oral composition for plaque, caries and calculus retardation with reduced staining tendencies. The bis-biguanides are described as useful and the problem, already recognized by the above cited British Patent, is acknowledged by Haefele. Consequently, Haefele teaches that a suitable sudsing agent will be one that will not react with the bis-biguanide compound, i.e. a non-soap nonionic, cationic, zwitterionic or amphoteric detergent will be suitable.

In accordance with Haefele, the bis-biguanides are combined with one or more of a long list of anticalculus agents including, for example, ammonium chlorides, water soluble salts of polycarboxylic acids, and polyphosphonates, all of which are, to varying degrees, anionic. Recognizing the possibility of association between the anionic anti-calculus agent and the cationic bis biguanide, Haefele teaches that when the bis biguanide selected is more soluble than the salt resulting from the association of bis biguanide with the anticalculus agent, then an excess of the anticalculus agent must be used or otherwise, the two will react leaving insufficient free anticalculus agent. Unfortunately, while it may be theoretically possible to add sufficient anticalculus agent in this manner so as to ensure an effective amount of such anticalculus agent unassociated with the cationic antimicrobial, the laws of chemical equilibrium being what they are, such excess anticalculus agent will deplete the composition of antimicrobial agent. In fact, when considering the problem generally, it will be recognized that because of the constraints imposed by equilibrium and mass action criteria, the degrees of freedom existing in such a system are insufficient to allow a formulation to combine the cationic antimicrobial with an anionic agent and arbitrarily select the effective concentration of both in the composition. Instead, one such concentrate may be selected and the laws of the system will dictate the other.

Accordingly, heretofore there has been no satisfactory method of insuring effective concentrations of both anionic agents and the cationic bis biguanide, therefor greatly limiting the wide use of these otherwise highly effective antimicrobial agents.

SUMMARY OF THE INVENTION

It has now been discovered that an oral composition may be provided and a method employed which allows the formulator to incorporate both the cationic bis biguanide antimicrobials and anionic agents in the composition while still having the degree of freedom to provide effective quantities of both. Specifically, an oral composition is provided comprising an antimicrobial antiplaque effective quantity of a bis biguanide compound and an effective quantity of an anionic active agent. In accordance with the teachings herein, the composition further comprises a betaine surfactant present in at least that quantity sufficient to prevent the precipitation of the bis biguanide-anionic agent salt but in a quantity less than that which significantly affects the antimicrobial activity of the bis-biguanide compound. Generally this quantity of betaine, expressed as the weight ratio of betaine to the bisguanide compound (BBR) should vary between the minimum BBR, as determined, for the anion present in the oral composition, and less than about 8. Preferably, the BBR varies from 1.2 times the minimum to about 5. The minimum BBR is easily measured, for a given composition, by the method taught hereinafter.

The inclusion of the betaine surfactant in the relatively narrow range of concentrations prescribed herein has been discovered to allow for effective employment of both the anionic agent and the cationic antimicrobial. The precise mechanisms is not clearly understood but the following theory seems to fit those facts which have been empirically observed. Firstly, it is clear that the betaine surfactant micelles formed in the oral composition and the cationic antimicrobial associate together to some degree such that there is a dynamic equilibrium established between the surfactant associated cationic antimicrobial and the free aqueous phase cationic antimicrobial. Experiments directed toward separating associated from unassociated antimicrobial have confirmed this relationship. Moreover, this association established between the surfactant and the antimicrobial seems to protect the antimicrobial from alternative association with the anionic agent in the solution. Conceptually, it appears that the affinity of the antimicrobial to associate with the betaine surfactant micelles is significantly greater than that of association with the anionic agent and hence the addition of betaine to the mixture retards and, at a relatively low level of addition, precludes the precipitation of cationic antimicrobial-anionic salts. It has also been observed that at levels of betaine addition which so preclude such precipitation, the unassociated-associated antimicrobial system still maintains essentially all of its efficacy as an antimicrobial agent. Again, conceptually, this may be thought of as resulting from the affinity of th antimicrobial agent to receptor sites on the target microbes being greater than the affinity of the antimicrobial agent to associate with the betaine micelle. Alternatively, this could result from the possibility that the association of the antimicrobial with the betaine micelle does not block the operative receptor sites of the antimicrobial.

To some degree, the former theory is favored in that it has been further discovered that while a significant concentration range for the betaine exist whereby the anionic-antimicrobial salt will not precipitate and the antimicrobial is still effective, a point is reached wherein the further increase in betaine concentration reduces the availability of the antimicrobial.

Irrespective the reasons, there is a window of betaine concentration in which both the anionic and the cationic may operate effectively by virtue of the presence of the betaine surfactant. Surprisingly, this situation does not exist for some of the art suggested surfactants. Thus, for example, to prevent the antimicrobial-anionic salt precipitate, cationic surfactants must be provided in such a system at a concentration level so high as to inactivate the antimicrobials i.e. the window of concentration is always shut. The same condition applies to nonionic surfactants. It is therefore surprising that only the ampholyte betaine offers the window of opportunity wherein both precipitation inhibition and activity prevail. Moreover, even in those prior art suggestions which included in their broad teachings of the use of nonanionics and antimicrobial among others the use of ampholytics such as betaine, the suggested concentration of surfactant range above that being suggested herein.

DETAILED DESCRIPTION OF THE INVENTION

The invention comprises providing an aqueous oral composition comprising a bis biguanide antimicrobial agent, at least one anionic active agent and the selection of a betaine as the surfactant in such composition, with the betaine being provided in a narrowly prescribed range of concentrations.

The bis biguanides usable in accordance with this invention have the generic formula

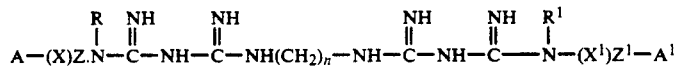

wherein A and $A^1$ each represent either (1) a phenyl radical which optionally is substituted by an alkyl or alkoxy group containing from 1 to about 4 carbon atoms, a nitro group, or a halogen atom; (2) an alkyl group containing from 1 to about 12 carbon atoms; or (3) alicyclic groups containing from 4 to about 12 carbon atoms; wherein X and $X^1$ each represent an alkylene radical containing from 1 to 3 carbon atoms; wherein Z and $Z^1$ each can be either 0 or 1; wherein R and Reach represent either hydrogen, or alkyl radical containing from 1 to about 12 carbon atoms, or an aralkyl radical containing from 7 to about 12 carbon atoms; wherein n is an integer from 2 to 12 inclusive; and wherein the chain $(CH_2)_n$ may optionally be interrupted by oxygen or sulfur atoms, aromatic nuclei, etc. Usable water soluble salts of the above are chloride, bromides, sulfates, alkyl sulfonates such as methyl sulfonate and ethyl sulfonate, phenylsulfonates such as p-methylphenyl sulfonates, nitrates, acetates, gluconates, etc.

Examples of suitable bis biguanide compounds are 1,6-bis-(2ethylhexylbianidohexane)dihydrochloride; 1,6-di-($N_1$, $N_1'$-phenyldiguanido-$N_5,N_5'$)-hexane tetrahydrochloride; 1,6-di-($N_1$, $N_1$, -phenyl-$N_1$, $N_1'$-methyldiguanido-$N_5,N_5'$)-hexane dihydrochloride; 1,6-di ($N_1$, $N_1'$-o-chlorophenyldiguanido-$N_5$, $N_5'$)-hexane dihydrochloride; 1,6-di[$N_1$, $N_1'$-p-methoxyphenyl)

diguanido-N$^e$ N$_5$,N$_5'$)-hexane dihydrochloride; 1,6-di[N$_1$, N$_1'$-methyl-phenyl) diguanido-N$_5$N$_5'$]-hexane dihydrochloride; w:w-di-(N$_1$, N$_1'$-phenyldiguanido-N$_5$, N$_5$)-di-n-propylether dihydrochloride; w:w-di(N$_1$, N$_1'$-2,4-dichlorophenyldiguanido-N$_5$, N$_5'$)hexane tetrahydrochloride; 1,6-di[N$_1'$-p-methylphenyldiguanido-N$_5$, N$_5'$)hexane dihydrochloride; 1,6-di(N$_1$, N$_1'$-2,4,5-trichlorophenyldiguanido-N$_5$, N$_5'$) hexane tetrahydrochloride; 1,6-di [N$_1$, N$_1'$-p-chlorophenyldiguanido-N$_5$, N$_5'$) m-xylene dihydrochloride; w:w'di(N$_1$, N$_1'$-p-chlorophenyldiguanido-N$_5$, N$_5'$)m-xylene dihydrochloride; 1,12-di(N$_1$, N$_1'$-p-chlorophenyldiguanido-N$_5$, N$_5'$) dodecane dihydrochloride; 1,10-di(N$_1$, N$_1'$-phenyldiguanido-N$_5$, N$_5'$) decane tetrahydrochloride; 1,12-di(N$_1$, N$_1'$-phenyldiguanido-N$_5$, N$_5'$)dodecane tetrahydrochloride; 1,6-di (N$_1$, N$_1'$o-chlorophenyldiguanido-N$_5$, N$_5'$) hexane dihydrochloride; 1,6-di(N$_1$N$_1'$-p-chlorophenyldiguanido-N$_5$, N$_5'$)-hexane tetrahydrochloride; ethylene bis (1-tolyl biguanide); ethylene bis (p-tolyl biguanide); ethylene bis(3,5-dimethylphenyl biguanide); ethylene bis(p-tert-amylphenyl biguanide); ethylene bis(nonylphenyl biguanide); ethylene bis (phenyl biguanide); ethylene bis (N-butylphenyl biguanide); ethylene bis (2,5-diethoxyphenyl biguanide); ethylene bis(2,4-dimethylphenyl biguanide); ethylene bis(o-diphenylbiguanide); ethylene bis(mixed amyl naphthyl biguanide); N-butyl ethylene bis(phenyl biguanide); trimethylene bis(o-tolyl biguanide); N-butyl trimethylene bis(phenyl biguanide); tetramethylene bis(1-tolyl biguanide); the specific compounds disclosed in U.S. Pat. No. 2,863,919, Birtwell et. al., (Dec. 9, 1958), said patent being incorporated herein by reference; the specific compounds disclosed in U.S. pat. No. 3,468,898, Cutler et. al., (Sept. 23, 1969), said patent being incorporated herein by reference; and the corresponding pharmaceutically acceptable salts of all of the above such as the acetates; gluconates; hydrochlorides; hydrobromides; citrates; bisulfites; fluorides; polymaleates; N-coconutalkyl sarcosinates; phosphites; hypophosphites; perfluorooctanoates; silicates; sorbates; salicylates; maleates; tartrates; fumarates; ethylenediaminotetraacetates; iminodiacetates; cinnamates; thiocyanates; arginates; pyromellitates; tetracarboxybutyrates; benzoates; glutarates; monofluorophosphates; and perfluoropropionates.

The antibacterial bis biguanide of choice is the digluconate of chlorhexidine i.e. 1,1'-hexamethylene-biss-(4-chlorophenyl)-biguanide]. Preferably, chlorhexidine digluconate is present in the oral compositions of this invention in a quantity ranging from about 0.01 to about 5% by weight of the oral composition and more preferably from about 0.01 to about 3% by weight of the oral composition.

The anionic active ingredient may take many forms and be provided for a variety of functional purposes. For example, anionic active agents may be provided to impart anticaries properties, antitartar or calculus properties, anti-staining properties or the like. Frequently, the same anionic may provide two or more such properties or, in the alternative, more than one anionic may be employed.

Anionic agents imparting anticaries properties are typically a fluorine-providing compound partially or totally soluble in water. Among these materials are inorganic fluoride salts, such as soluble alkali metal, alkaline earth metal and heavy metal salts, for example, sodium fluoride, potassium fluoride, ammonium fluoride, a copper fluoride such as cuprous fluoride, zinc fluoride, a tin fluoride such as stannic fluoride or stannous chlorofluoride, barium fluoride, sodium fluorosilicate, ammonium fluorosilicate, sodium fluorozirconate, sodium monofluorophosphate, aluminum mono- and di-fluorophophate, and fluorinated sodium calcium pyrophosphate. Alkali metal and tin fluorides, such as sodium and stannous fluorides, sodium monofluorophosphate and mixtures thereof, are preferred.

The amount of the fluorine-providing compound is dependent to some extent upon the type of compound, its solubility, and the type of oral preparation, but it must be a nontoxic amount. In a solid oral preparation, such as toothpaste or toothpowder, an amount of such compound which releases a maximum of about 1% by weight of the preparation is considered satisfactory. Any suitable minimum amount of such compound may be used, but it is preferable to employ sufficient compound to release about 0.005 to 1%, and preferably about 0.1% of fluoride ion. Typically, in the cases of alkali metal fluorides and stannous fluoride, this component is present in an amount up to about 2% by weight, based on the weight of the preparation, and preferably in the range of about 0.05 to 1%. In the case of sodium monofluorophosphate, the compound may be present in an amount up to 7.6% by weight, more typically about 0.76%.

In a liquid oral preparation such as a mouthwash, the fluorine-providing compound is typically present in an amount sufficient to release up to about 0.13%, preferably about 0.0013 to 0.1% and most preferably about 0.0013 to 0.05%, by weight, of fluoride ion.

Anionic agents imparting antitartar or anticalculus properties are salts of a wide range of anticalculus agents suggested in the prior art and set out in detail in U.S. Pat. No. 4,515,772 and 4,885,155. Such agents may include for example anionic forms of a chelating agent such as ethylenediamine tetracetic acid, nitrilotriacetic acid, certain polyphosphates and fluorides, certain carboxyl diphosphonates. The anticalculus agents of choice currently are the active soluble metaphosphates or pyrophosphates and in particular the alkali metal salts thereof.

Anionic agents imparting stain quenching properties have also been suggested by the prior art and are usable herein. Such components may include the anionic forms of zinc phenol sulfonate hydroxy quinoline, homopolymer and copolymers of aliphate polycarboxylate oils, certain polyphosphates certain salts of rare earth metals, phytic acid and certain polyphosphonates and ammonium polyphosphates. Also usable is the anionic salts of polymeric polyphosphonic compound such as polyalkyl bis-(phosphono methylene) amino acid, as suggested in U.S. Pat. No. 4,042,679 to Gaffar; a 1-phosphono propanetricarboxylic acid or a 2-phosphono-butane-1,2,4-tricarboxylic acid, as suggested in U.S. Pat. No. 4,224,309 to Gaffar, et al; and a phosphonacetic acid as suggested in U.S. Pat. No. 4,118,474 to Gaffar et al. of particular interest are the anionic salts of an azacyclo alkane diphosphonic acid such as, for example, azacyclohexane-2,2-diphosphonic acid, as is described in the commonly assigned U.S. Pat. application Ser. No. 594,598 filed on the same day as this by Gaffar and Polefka and entitled "Non-Staining Antibacterial Oral Composition".

In accordance with the teachings herein, the bis-biguanide and the anionic agents are combined with a narrowly prescribed quantity of a betaine surfactant. The betaine component has the general formula:

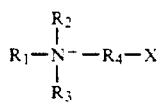

wherein:

$R_1$ is an alkyl group having 8 to about 20 carbon atoms and preferably 12 to 16 carbon atoms or the alkyl amido group having the formula

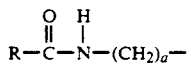

wherein R is an alkyl group having from about 8 to 20 carbon atoms and preferably 12 to 16 carbon atoms and a is the integer 1 to 3;

$R_2$ and $R_3$ are each alkyl group having 1 to 3 carbon atoms and preferably 1 carbon atom;

$R_4$ is an alkylene or hydroxyalkylene group having from 1 to 4 carbon atoms and, optionally, one hydroxyl group; and X is a carboxylate, sulfonate or phosphonate group. Typical alkyl dimethyl betaines include decyl betaine or 2-(N-decyl-N, N-dimethylammonio) acetate, coco betaine or 2-(N-coco-N, N-dimethyl ammonio) acetate, myristyl betaine, palmityl betaine, lauryl betaine, cetyl betaine, stearyl betaine, etc. The amidobetaines are exemplified by cocoamidoethyl betaine, cocoamidopropyl betaine, lauramidopropyl betaine and the like. The betaines of choice are preferably the cocoamidopropyl betaine and, more preferably, the lauramide propyl betaine.

In accordance with the teachings of this invention, the betaine is present in the oral composition in a quantity at least sufficient to prevent the precipitation of the bis biguanide-anionic agent salt. This quantity is referred to herein as the minimum ratio, by weight, of betaine to cationic antimicrobial compound which will preclude anionic-cationic salt precipitation (the minimum BBR) and is determined by the following procedure.

To determine the minimum BBR necessary to prevent chlorhexidine-anion precipitation, for example, stock solution containing 0.24% (w/w) chlorhexidine digluconate were prepared to contain the following betaine concentrations (w/w) 0.00%, 0.10%, 0.20%, 0.30%, 0.40%, 0.50%, 0.60%, 0.70%, 0.80%, 0.90%, 1.00%, 1.10%, and 1.20%. A 1 ml aliquot of each solution was transferred to test tubes containing an equal volume of a 1-2% (w/w) solution of the test anion (pH 7.0). After mixing and an overnight incubation at room temperature, the samples were viewed for precipitation. The lowest concentration of betaine inhibiting precipitation is obtained and the ratio of betaine to chlorhexidine in such concentration is calculated as the minimum BBR. Examples are given in the following table:

TABLE 1

| Minimum BBR Inhibiting Chlorhexidine-Anion Precipitation | | |
|---|---|---|
| Anion | Function | Min. BBR (wt./wt.) |
| Phosphonoproponate Tricarboxylic Acid | Anticalculus/ Stain Quencher | 1.25 |
| Phosphonobutane Tricarboxylic Acid | Anticalculus/ Stain Quencher | 0.42 |
| Potassium Pyrophosphate | Anticalculus/ Stain Quencher | 1.04 |
| Sodium Hydrogen Phosphate | Continament of Pyrophosphate | 0.63 |

TABLE 1-continued

| Minimum BBR Inhibiting Chlorhexidine-Anion Precipitation | | |
|---|---|---|
| Anion | Function | Min. BBR (wt./wt.) |
| Sodium Saccharin | Sweetener | 1.25 |
| Sodium Monofluorophosphate | Fluoride Source | 0.83 |

Preferably, the betaine is present in the oral composition in a quantity of at least 1.2 times the minimum BBR.

Further, in accordance with the teachings herein, the betaine quantity, expressed as BBR, must be less than that which will significantly decrease the efficacy of the antimicrobial agent. Accordingly, this ratio should not exceed 8.0 and preferably should not exceed 5.0. To illustrate the significance of the restriction in betaine quantity, the following experiment was performed. A series of aqueous solutions of 0.12%, by weight of chlorhexidine gluconate were prepared with varying quantities of betaine. The antiplaque activity of the solutions were measured by a modified in vitro plaque assay. Extracted, non-carious human incisors were cleaned of gross deposits and polished with pumice using a dental drill. The root surface was removed at the cemento-enamel junction and the enamel portion of the tooth was attached to nichrome wire with the aid of epoxy. Each tooth was suspended from a cap(10 dram vial) such that the tooth was completely submerged when the vial contained 10 ml of distilled water. The teeth were sterilized by irradiation with UV light for 2 hr. After sterilization the teeth were treated for 30 sec. with the test solution, washed extensively with Resting (Saliva Salts Buffer (1.1 mMCaCl$_2$, 0.6mM KH$_2$PO$_4$, 50mM NaCl--pH 7.0), and transferred aseptically to vials containing 10 ml Trypticase Soy broth (Difco) with 5% sucrose which had been pre-inoculated to a high cell density with an 18 hr. culture of Actinomyces viscous T14v and Streptococcus mutans 6715. After 24 hr. of plaque development, the teeth were retreated with the test rinses and then transferred to a new vial pre-inoculated with bacteria. The treatment and plaque growth procedure was repeated for four successive days at which time plaque was removed from the teeth by exposing the plaque covered teeth to sonic energy. Plaque was quantified by measuring bacterial deoxyribonucleic acid (DNA) associated with each tooth according to the fluorescence DNA assay of Paul, J.H. and Myers, B. (1982) Fluorometric Determination of DNA in Aquatic Microorganisms by Use of Hoechst 33258, Appl. Environ. Microbiol. 43:1393-13999. The results are as shown in Table 2, below.

TABLE 2

| Antiplaque Activity of 0.12% Chlorhexidine Gluconate As a function of Betaine Concentration | | |
|---|---|---|
| Betaine to Chlorhexidine Ratio (BBR) | Plaque DNA (ug/Tooth) | % Reduction in Plaque |
| 0.0 | 2.1 ± 1.0 | 100.00 |
| 2.08 | 4.9 ± 1.1 | 83.6 |
| 4.17 | 6.2 ± 0.9 | 76.0 |
| 6.25 | 7.1 ± 1.5 | 70.5 |
| 8.23 | 8.3 ± 6.4 | 63.7 |
| 12.50 | 5.9 ± 2.0 | 77.8 |
| Control (water only) | 19.2 ± 1.7 | — |

The percent reduction in plaque is based on the sample containing no betaine as the standard. As can be seen from the above table, at values of BBR above 8, the percent reduction in plaque drops significantly. The rise in percent reduction in plaque at the very high BBR level of 12.5 is believed to be due to the bacterial inhibiting properties of the betaine itself masking the chlorhexidine inhibiting properties of the betaine. Unfortunately, such high levels of betaine are unusable in oral compositions for organoleptical and safety reasons.

To further illustrate the embodiments of this invention, the following Examples are provided:

EXAMPLE 1

A series of mouthrinse compositions are prepared to have the formulas set out in Table 3 below:

TABLE 3

| | Sample | | |
|---|---|---|---|
| | A | B | C |
| Ingredients (weight %) | | | |
| Chlorhexidine gluconate | 0.12 | 0.12 | 0.12 |
| Tego-betaine | 0.25 | 0.25 | 0.00 |
| 1-phosphonopropane 1,2,3-tricarboxylic acid (PPT) | 0.50 | 0.0 | 0.50 |
| 2-phosphonobutane 1,2,4-tricarboxylic acid (PBTA) | 0.0 | 0.5 | 0.0 |
| Sodium Saccharin | 0.1 | 0.1 | 0.1 |
| Glycerine | 10.0 | 10.0 | 10.0 |
| Flavor | 0.04 | 0.04 | 0.04 |
| Water to Q.S. | | | |
| | 100.00 | 100.00 | 100.00 |

To prepare these mouthrinses, the betaine and chlorhexidine gluconate are admixed in one-half of the total volume of distilled water. With mixing, the PPT or the PBTA, if present, is added. The sequence of additives is important; the betaine and chlorhexidine must be premixed prior to the addition of the anionic ingredients. The pH of the mouthrinse is adjusted to 5.7 with 6N sodium hydroxide and/or glacial acetic acid. Finally, the remaining ingredients are added.

Example 2

The sample mouthrinses set out above are tested for stability by four week accelerated aging at the temperatures set out in Table 4, below:

TABLE 4

Stability of Mouthrinses

| | | Percent Recovery (wt. %) | | |
|---|---|---|---|---|
| Sample | Aging Temp. (°C.) | Chlorhexidine | Phosphonate | Physical Appearances |
| A-Chlor/Bet/PPT | 20 | 96 | 97 | clear solutions |
| A-Chlor/Bet/PPT | 49 | 95 | 96 | clear solutions |
| B-Chlor/Bet/PBTA | 20 | 96 | 103 | clear solutions |
| B-Chlor/Bet/PBTA | 49 | 95 | 102 | clear solutions |
| C-Chlor/PPT | 20 | 6% | — | precipitated |

In the above study, the concentration of the chlorhexidine is measured by the method of Huston, C.E., et al. (J. Chromato 237 (1982) 457–464) and the monophosphate tricarboxylate anions are determined by Dionex chromatography. Rinse A and B, containing the herein prescribed quantity of betaine, exhibited excellent stability at both temperatures, Rince C, without the betaine, produced an unusable precipitated rinse.

EXAMPLE 3

The antiplaque activity of the rinses are measured by the in vitro assay described above in conjunction with Table 2. The control comprises a water-only rinse and the standard for percent reduction is set by the 0.12%, by weight, aqueous chlorhexidine solution The results are set out in the Table 5 below:

TABLE 5

Plaque Reduction of Rinses

| Sample | Number | Plaque DNA Recovered (ug/tooth + SD) | Percent Reduction (%) |
|---|---|---|---|
| Water Control | 4 | 103 ± 4.0 | — |
| Chlorhexidine Standard | 4 | 17 ± 3 | 83.5 |
| A-Chlor/PPT/Bet | 4 | 22 ± 14 | 78.6 |
| B-Chlor/PBTA/Bet | 4 | 14 ± 3 | 86.4 |
| C-Chlor/PPT | 4 | 83 ± 31 | 19.4 |

As the above data show, the chlorhexidine/betaine/PPT and chlorhexidine/betaine/PBTA rinses are as effective as the chlorhexidine standard solution in reducing plaque. However, in the absence of the betaine, the chlorhexidine and the PPT anion of rinse C precipitate, drastically reducing the antiplaque activity of the chlorhexidine.

Example 4

A dentifrice composition is prepared having the formula set out in Table 6, below:

TABLE 6

| Ingredient | Percent by Weight (%) |
|---|---|
| Chlorhexidine gluconate | 0.90 |
| Tego-betaine | 1.00 |
| Polyethylene glycol (PEG-600) | 11.00 |
| Hydroxethylcellulose | 1.00 |
| Phosponate anion (PBTA or PPT) | 2.00 |
| Hydrated Alumina | 52.00 |
| Sodium Saccharin | 0.30 |
| Flavor | 1.10 |
| Sodium Fluoride | 0.24 |
| Deionized Water | Q.S. |
| | 100.00 |

The dentifrice exhibits excellent stability and the chlorhexidine maintains its antibacterial activity.

What is claimed is:

1. An oral composition consisting essentially of 0.01 to about 5.0% by weight of a plaque reducing cationic bisbiguanide antibacterial agent and an effective quantity of a fluorine-providing anionic agent, the anionic agent being present in an amount sufficient to release from about 0.005 up to 1% by weight fluoride ion, said cationic and anionic agents being stabilized by a precipitation-inhibiting quantity of a betaine surfactant, said betaine surfactant being present in a quantity in which the weight ratio of betaine to bisguanide (BBR) is effective to prevent precipitation and insufficient to decrease the efficacy of the plaque-reducing activity of said cationic bis-guanide antibacterial agent, the BBR ranging from the minimum BBR to a BBR of less than about 8.

2. The composition of claim 1 wherein the betaine surfactant is present in a quantity relative to the antibacterial agent which ranges from the minimum BBR to a BBR of less than about 8.

3. The composition of claim 1 wherein the BBR ranges from about 1.2 times the minimum BBR to a BBR of about 5.

4. The composition of claim 1 wherein the antibacterial agent has the generic formula

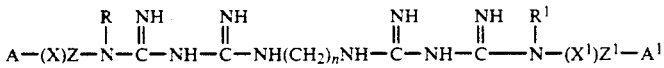

wherein A and A¹ each represent either (a) a phenyl radical which optionally is substituted by an alkyl or alkoxy group containing from 1 to about 4 carbon atoms, a nitro group, or a halogen atom; (2) an alkyl group containing from 1 to about 12 carbon atoms; or (3) alicyclic groups containing from 4 to about 12 carbon atoms; wherein X and X¹ each represent an alkylene radical containing from 1 to 3 carbon atoms; wherein Z and $Z_1$ each can be either 0 or 1; wherein R and $R_1$ each represent either hydrogen, or alkyl radical containing from 1 to about 12 carbon atoms, or an aralkyl radical containing from 7 to about 12 carbon atoms; wherein n is an integer from 2 to 12 inclusive; and wherein the chain $(CH_2)_n$ may optionally be interrupted by oxygen or sulfur atoms, or an aromatic nuclei.

5. The composition of claim 1 wherein the betaine is cocoamidopropyl betaine.

6. The composition of claim 1 wherein the betaine is lauramidopropyl betaine.

7. A method for preparing an oral composition comprising about 0.1 to about 5.0% by weight of a plaque-reducing quantity of a cationic bis-biguanide antibacterial agent and an effective quantity of anionic agent and a stabilizing precipitation- inhibiting quantity of a betaine surfactant, the betaine surfactant being present in a quantity in which the weight ratio of betaine to bisbiguanide is effective to prevent precipitation and insufficient to decrease the efficacy of the plaque-reducing activity of the cationic bis-biguanide antibacterial agent comprising:

providing a first part of said composition comprising said quantity of cationic antibacterial agent, said first part being substantially free of said anionic agent;

combining said first part with a precipitation-inhibiting quantity of a betaine surfactant to form betaine micelles associated with said antibacterial agent;

providing a second part of said composition comprising said quantity of anionic agent, said second part being substantially free of said cationic antibacterial agent; and combining said first part containing the associated betaine micelle antibacterial agent with the second part to form the composition 8. The method of claim 7 wherein the betaine surfactant is provided in a quantity relative to the antibacterial agent which ranges from the minimum BBR to a BBR of less than about 8.

9. The method of claim 8 wherein the BBR ranges from about 1.2 times the minimum BBR to a BBR of about 5.

10. The method of claim 7 wherein the antibacterial agent has the generic formula

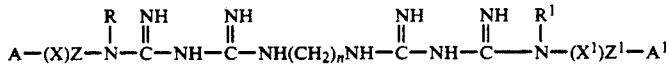

A and A¹ each represent either (1) a phenyl radical which optionally is substituted by an alkyl or alkoxy group containing from 1 to about 4 carbon atoms, a nitro group, or a halogen atom; (2) an alkyl group containing from 1 to about 12 carbon atoms; or (3) alicyclic groups containing from 4 to about 12 carbons atoms; wherein X and X¹ each represent an alkylene radical containing from 1 to 3 carbon atoms; wherein Z and Z¹ each can be either 0 or 1; wherein R and R¹ each represent either hydrogen, or alkyl radical containing from 1 to about 12 carbon atoms, or an aralkyl radical containing from 7 to about 12 carbon atoms; wherein n is an integer from 2 to 12 inclusive; and wherein the chain $(CH_2)_n$ may optionally be interrupted by oxygen or sulfur atoms or an aromatic nuclei.

11. The method of claim 7 wherein the betaine is cocoamidopropyl betaine.

12. The method of claim 7 wherein the betaine is lauramidopropyl betaine.

* * * * *